United States Patent
Pagnoulle et al.

(10) Patent No.: US 11,109,958 B2
(45) Date of Patent: Sep. 7, 2021

(54) POSTERIOR CHAMBER PHAKIC INTRAOCULAR LENS

(71) Applicant: PhysIOL, Angleur (BE)

(72) Inventors: Christophe Pagnoulle, Verviers (BE); Suad Redzovic, Jupille sur Meuse (BE)

(73) Assignee: PhysIOL, Angleur (BE)

( * ) Notice: Subject to any disclaimer, the term of this patent is extended or adjusted under 35 U.S.C. 154(b) by 0 days.

(21) Appl. No.: 16/434,696

(22) Filed: Jun. 7, 2019

(65) Prior Publication Data

US 2020/0375727 A1  Dec. 3, 2020

(30) Foreign Application Priority Data

May 29, 2019  (BE) .................... 2019/5356

(51) Int. Cl.
*A61F 2/16*  (2006.01)

(52) U.S. Cl.
CPC ............ *A61F 2/161* (2015.04); *A61F 2/1601* (2015.04); *A61F 2/1613* (2013.01); *A61F 2/1605* (2015.04); *A61F 2002/1681* (2013.01); *A61F 2002/1689* (2013.01); *A61F 2220/0008* (2013.01); *A61F 2250/0053* (2013.01)

(58) Field of Classification Search
CPC .. A61F 2/1601; A61F 2/16015; A61F 2/1605; A61F 2/161; A61F 2002/1689; A61F 2002/169

See application file for complete search history.

(56) References Cited

U.S. PATENT DOCUMENTS

| | | | |
|---|---|---|---|
| 4,547,914 A | 10/1985 | Castleman | |
| 4,673,539 A * | 6/1987 | Hammar | C08L 31/02 264/1.1 |
| 4,685,920 A | 8/1987 | Fritch | |
| 5,258,025 A * | 11/1993 | Fedorov | A61F 2/1602 623/6.36 |
| 6,749,633 B1 | 6/2004 | Lorenzo et al. | |
| 2005/0021140 A1 | 1/2005 | Liao | |
| 2005/0096741 A1 | 5/2005 | Cumming | |
| 2006/0095127 A1* | 5/2006 | Feingold | A61F 2/1602 623/5.15 |
| 2006/0100704 A1 | 5/2006 | Blake et al. | |
| 2006/0259140 A1 | 11/2006 | Dell | |
| 2007/0168028 A1 | 7/2007 | Tran et al. | |
| 2007/0244560 A1 | 10/2007 | Ossipov et al. | |
| 2008/0109078 A1* | 5/2008 | Rozakis | A61F 2/1613 623/6.43 |
| 2012/0310342 A1 | 12/2012 | Nguyen et al. | |

(Continued)

FOREIGN PATENT DOCUMENTS

| | | |
|---|---|---|
| EP | 0934038 A1 | 8/1999 |
| WO | 01/34066 A1 | 5/2001 |
| WO | 2008/051850 A2 | 5/2008 |

(Continued)

*Primary Examiner* — Leslie Lopez

(74) *Attorney, Agent, or Firm* — Christensen O'Connor Johnson Kindness PLLC

(57) ABSTRACT

A posterior chamber phakic intraocular lens comprising a central optical part, a peripheral haptic part comprising a plurality of support elements arranged to lie on a ciliary zonule of an eye, and at least one flexible haptic comprising a reticulated distal region arranged to lay into a ciliary sulcus of the eye.

20 Claims, 7 Drawing Sheets

(56) References Cited

U.S. PATENT DOCUMENTS

2012/0330415 A1 12/2012 Callahan et al.
2016/0095699 A1 4/2016 Zaldivar

FOREIGN PATENT DOCUMENTS

| WO | 2014/108100 A1 | 7/2014 |
| WO | 2014/167425 A1 | 10/2014 |
| WO | 2016/191614 A1 | 12/2016 |

* cited by examiner

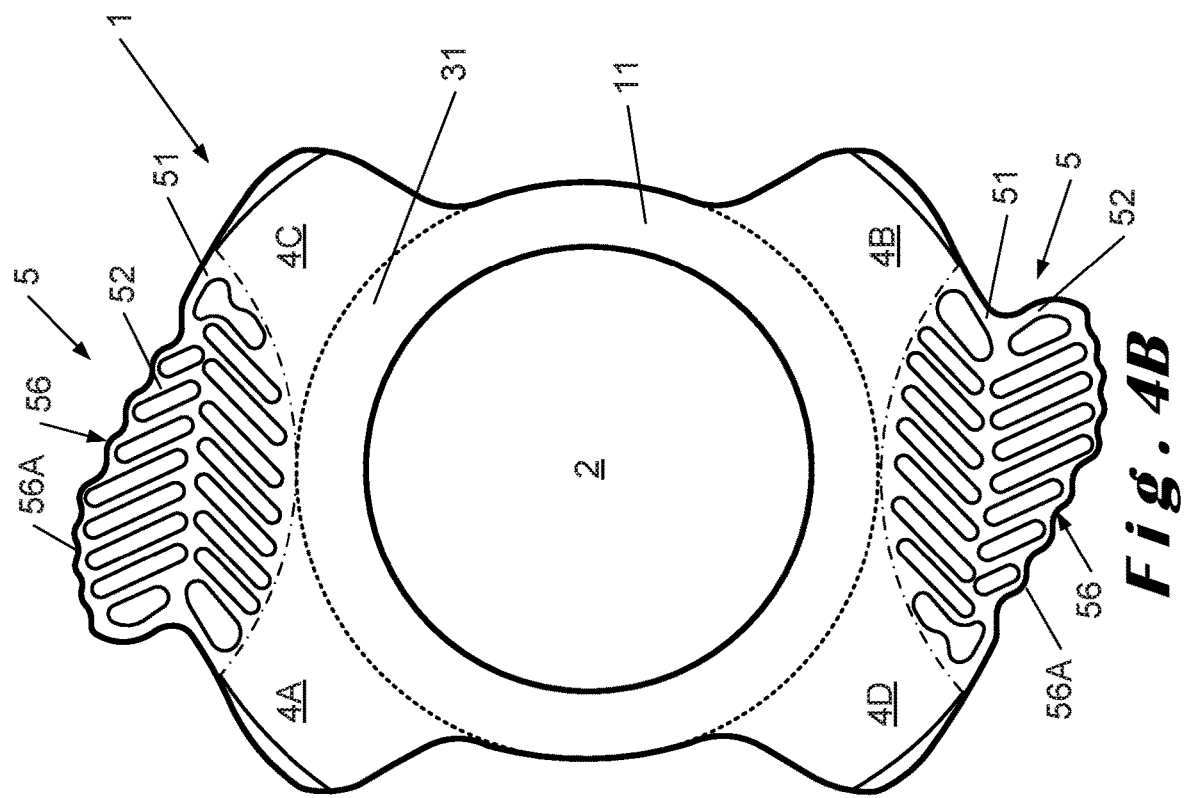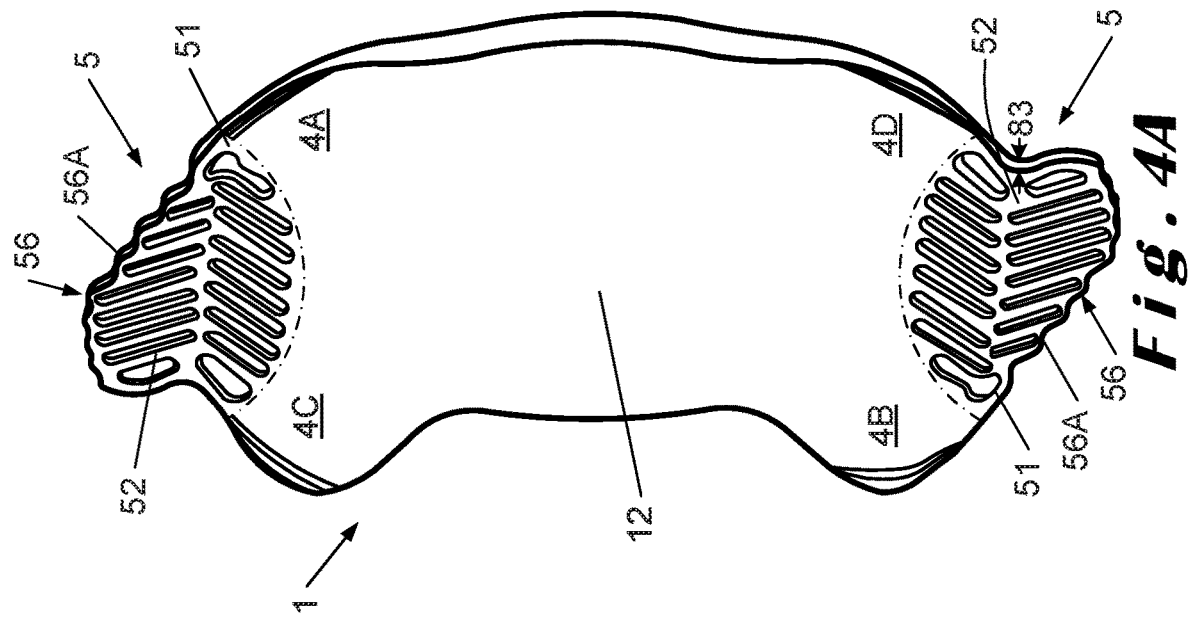

POSTERIOR CHAMBER PHAKIC INTRAOCULAR LENS

TECHNICAL FIELD

Embodiments of the present disclosure relate to an intraocular lens (IOL). More specifically, the present disclosure concerns a posterior chamber phakic intraocular lens.

BACKGROUND

Generally speaking, phakic intraocular lenses are intraocular lenses intended to be placed in an eye in order to correct defects of vision. These intraocular lenses are generally implanted in patients who are still young, as a complement to the human lens (i.e. the natural crystalline lens).

There are several classes of phakic intraocular lenses, among which those of posterior chamber phakic intraocular lenses intended to be implanted in an area of the eye between a posterior surface of the iris and an anterior surface of the lens, and at least partially in the ciliary sulcus of the eye.

A limit in implantation of such an intraocular lens lies in the fact that it is likely to be positioned differently from one eye to the other on the basis of some parameters, especially on the basis of the anatomy of the ciliary sulcus, the size of which usually varies by several millimeters from one patient to another. In particular, implantation of a posterior chamber phakic intraocular lens, the size of which may not be adapted, would risk leading to complications that would be more or less serious for a patient, such as:

for example, in a case where the phakic intraocular lens is too small with respect to the size of the patient's ciliary sulcus (or "sulcus-to-sulcus distance"): a contact of the intraocular lens with the human lens that has an impact on precision of vision or generates a cataract of the eye, or a loss in the corrective power of the phakic intraocular lens;

for example, in a case where the phakic intraocular lens is too large with respect to the size of the patient's ciliary sulcus: an inflammation, a depigmentation of the iris, a pupillary block, a glaucoma, and/or a depression between the anterior and posterior chambers of the eye after a pupillary block.

Production and use of several sizes of posterior chamber phakic intraocular lenses on the basis of the anatomy of the patient's eye cannot completely circumvent this defect. Indeed, shortcomings in terms of the stability of the position of such a phakic intraocular lens once it is implanted in an eye are likely to lead to the same medical complications.

SUMMARY

Embodiments of the present disclosure aim to provide a posterior chamber phakic intraocular lens that is adapted to any eye anatomy and is particularly stable in implantation position in an eye.

For this purpose or others, the disclosure provides an example of a posterior chamber phakic intraocular lens comprising:

an anterior surface and a posterior surface;
a central optical part comprising a lens, and extending radially relative to an optical axis directed from the anterior surface to the posterior surface;
a peripheral haptic part extending radially outward relative to the central optic part;
the peripheral haptic part comprising:
    a proximal portion extending circumferentially around the central optical part;
    a distal portion at least around the proximal portion and comprising a plurality of support elements extending both radially outward and posteriorly relative to the central optical part; the support elements being configured for supporting the phakic intraocular lens on a ciliary zonule when it is in normal use in a (phakic) eye;
the central optical part and the peripheral haptic part forming a (rigid) dome;
at least one flexible haptic (e.g., in one piece) comprising:
    a proximal region at least around the proximal portion of the peripheral haptic part;
    a (reticulated) distal region at least around the proximal region and comprising a plurality of elongated flexible footplates that:
        extend at least partially radially outward relative to the central optical part, and that
        border cavities extending between the anterior and posterior surfaces;
a first diameter of the intraocular lens being strictly greater than a second diameter of an optical assembly consisting of the central optical part and the peripheral haptic part, measured perpendicularly to the optical axis;
at least one of the elongated flexible footplates extending substantially between the second and first diameters;
the distal region comprising a distal border connecting (mechanically) at least two of the elongated flexible footplates, and
the distal border being configured for stabilizing the intraocular lens into a ciliary sulcus when it is in normal use in a (phakic) eye.

The posterior chamber phakic intraocular lens provided by some embodiments of the present disclosure comprises a central optical part equipped with two distinct and complementary haptic structures: the peripheral haptic part comprising the plurality of support elements, and the at least one flexible haptic ("the flexible haptic" hereafter, although there are preferably at least two of such flexible haptics). The technical effect of the disclosure lies mainly in the combination of a structure in the form of a (rigid) dome of the optical assembly, the support elements of which are feet of the dome, supporting the phakic intraocular lens, for example the optical assembly, on the ciliary zonule, and the capacity of the flexible haptic to lay (and/or stabilize itself) into an arbitrary ciliary sulcus given that they extend radially beyond the optical assembly, and that the first diameter is strictly larger than the second diameter. These combined two haptic structures allow improved stabilization, both axial (along the eye optical axis or very close to) and radial (in an orthogonal direction with respect to the eye optical axis or very close to) as well as in rotation (around the eye optical axis or very close to), of the phakic intraocular lens in a implantation site defined in a posterior chamber of an eye, as well as adaptability of the phakic intraocular lens to a broad range of patient eye anatomies, one size fitting all patients anatomies.

For example, the peripheral haptic part allows stabilization of the implant in a direction parallel to the optical axis. The support elements are in secant planes with respect to a plane tangent to the central optical part, in a way to support the dome on the ciliary zonule in implantation position. The dome typically comprises a smooth posterior surface and is configured to be anteriorly above a human lens when the phakic intraocular lens is in normal use in an eye, so that it encloses the lens at least anteriorly. As a consequence, the distance, called "the vault", measured along the optical axis, between the human lens anterior surface and the posterior surface of the phakic intraocular lens, is defined and stabilized. It can be assimilated to a safety distance required in order to avoid a contact or too much proximity between the phakic intraocular lens and the lens, which would be likely to lead to physical trauma and medical complications, such as a human lens cataract. A "safety distance" between the phakic intraocular lens and the iris is also defined and stabilized as being the distance between the anterior surface of the phakic intraocular lens, in other words, the top of the dome, and the posterior surface of the iris conceived as a virtual iris plan occupying the pupil eye (in rise opening).

In some embodiments, this distance, called "the vault", is comprised and/or is adjustable between 100 and 1000 microns, more preferably between 350 and 700 microns, with or without radial and/or axial compression. This distance advantageously makes it possible to guarantee enough space between the phakic intraocular lens and both the lens and the iris, and to compensate for an anatomical size defect in the posterior chamber of the eye, or a possible positioning defect of the phakic intraocular lens, to sharply reduce the risks of complication for the patient. According to an embodiment of the disclosure, this distance is titrated by sculpting the posterior surface of the phakic intraocular lens such that it follows a contour of a specific natural crystalline lens for which it is intended to be implanted.

The structure of the rigid dome of the optical assembly is designed to adapt to any eye on the basis of the dome curvature, the posterior surface of which is preferentially more curved than the anterior surface of any lens, and on the basis of the choice of the second diameter, for example between 11 and 12 mm, and in some embodiments with a value of 11.25 mm to be compatible with a standard posterior chamber anatomy of an eye. So the rigid dome structure induced by the optical assembly is above the lens while being appropriately implanted in the posterior chamber of the eye, resting on the ciliary zonule, and stabilizing the phakic intraocular lens parallel to the optical axis. The flexible haptic extend further radially than the optical assembly in the posterior chamber of the eye, and lay into the ciliary sulcus. The flexibility and the geometry of this haptic make it possible to compensate for the size variations of the ciliary sulcus, so that the phakic intraocular lens in implantation position adapts itself perfectly to the size of the ciliary sulcus, across a range of internal eye dimensions including those which cannot be accurately estimated preoperatively, thereby potentially reducing the size of the first diameter of the phakic intraocular lens when it is in normal use in the eye, namely when it is in an implantation position in an eye, while maintaining a dome-shaped optical assembly with a dimension corresponding essentially to the second diameter. Therefore, and advantageously, the production and the handling of a single phakic intraocular lens model according to the disclosure are enough for a broad range of patient eye anatomies.

Moreover, the flexible haptic enables the stabilization of the phakic intraocular lens according to the disclosure in rotation in a plane perpendicular to the optical axis such that the variation in the internal sulcus diameter (acknowledged to be greater in one orientation than another because of an "oval" shape) can be fully compensated. This flexible haptic (preferably, at least two flexible haptics) is radially and circumferentially extended to lay (and/or hook and/or stabilize itself) into the ciliary sulcus of the eye, playing a role of circumferential anchors for the phakic intraocular lens, like a plane elastic fabric mounted laterally using lateral stabilizers. For example, this flexible haptic is important in the embodiment where the lens is that of a toric implant comprising an optic with a cylinder to correct astigmatism. In this case, the stability of the angular position of the lens in the perpendicular plane, called "rotational stability", is crucial in order to guarantee the expected optical results. The flexible haptic also contributes to stabilize the phakic intraocular lens in the aforementioned perpendicular plane when it is in normal use, as well as avoiding possible decentering of the phakic intraocular lens with respect to the optical axis of the eye, which could affect the expected optical results. The flexible haptic allows to maintain the lens in a central optical zone.

Beyond the combination of the two complementary haptic structures comprising both the plurality of support elements and the (at least one) flexible haptic, and allowing to achieve the technical effect of stability of the claimed phakic intraocular lens, the very specific and particular geometry of the distal region of the flexible haptic is also fully part of the present disclosure. This is discussed below.

In the framework of the present disclosure, the term "reticulated" has to be interpreted classically as having a geometry mimicking a net. Following this definition, as a consequence of the definition of the disclosure, the distal region of the flexible haptic is necessarily reticulated in the sense that it comprises a collection of the "reticles", for example interlacing reticles, forming a net. The reticles of the distal region comprise at least the elongated flexible footplates and the distal border. These elongated flexibles footplates do not interlace together and/or on themselves in some embodiments and extend partially radially outward relative to the central optical part. The distal border is transverse to most of the elongated flexible footplates in some embodiments, and to all elongated flexible footplates in other embodiments. For example, the distal border interlaces the elongated flexible footplates, mimicking then a net. Moreover, there exist the cavities, for example open cavities, between these reticles, in such way that the reticles border these cavities. These (open) cavities can be interpreted equivalently as spaces empty of solid matter constituting the intraocular lens. This term "space" is more convenient than "hole" as these spaces are not specifically holes provided in a solid matter, for example. Nevertheless, this cannot exclude a production method of a phakic intraocular lens according to the disclosure by providing holes in a solid matter for defining reticles of the distal region. The verb "border" has to be interpreted as "border at least partially" given that a cavity is typically bordered by more than one reticle.

The flexibility of the flexible haptic is at least partially due to the "reticulated" geometry and/or to the flexibility of the elongated flexible footplates. In some embodiments, the proximal region is circumscribed in the second diameter, and the distal region extends radially between the second and the first diameter. The distal region is particularly flexible so that it allows a postoperatively stable implantation of the phakic intraocular lens in an eye independently of size variations of the ciliary sulcus. The at least one elongated flexible footplate extending between the first and second diameters acts as a flexible anchor for stabilizing the phakic intraocular lens into the ciliary sulcus of the eye. The distal border connects at least two of the elongated flexible footplates, one of them being, for example, the at least one elongated flexible footplate, which provides at least locally the distal region with the above-mentioned reticulated structure and contributes to the one-piece structure retention of the distal region. Preferably, the elongated flexible footplates comprise strictly more than one elongated flexible footplates extending between the first and second diameters, the distal extremities of which belongs to the distal border. In this case, the above-mentioned advantageous reticulated structure and one-piece structure retention are then improved.

It is particularly advantageous to provide such above-commented "reticulated" structure in some embodiments for the distal region in place of considering a single flexible footplate extending between the first and second diameters whose distal extremity is configured for laying into the ciliary sulcus. In fact, such a footplate alone would be difficult to see and to maneuver during an implantation process in an eye. This is because such a footplate would be long, clear and thin while the iris of the eye under which it has to be inserted is opaque. Moreover, such a footplate would flip very easily during the insertion under the iris, requiring then additional surgical manipulations for putting it into a wished implantation position in normal use in the phakic eye. These surgical manipulations are to be avoided because they constitute a risk for a patient health. Each such additional surgical manipulation increases, for example, the risk of touching the natural crystalline lens of the eye and, then, to generate a cataract of the eye. The use of such a single flexible footplate also would make any axis alignment correction very difficult as the footplate would tend to flip. This is critical in some embodiments where the lens is that of a toric implant for astigmatism correction. For all these reasons, it is much more practical to consider such a flexible footplate as a reticle of a reticulated distal region of a one piece flexible haptic. This advantageous reticulated structure allows to use such flexible footplate extending between the first and second diameters whose distal extremity is configured for laying into the ciliary sulcus while overcoming the above-mentioned drawbacks as a whole reticulated region is much easier to see and to maneuver during an implantation process in an eye, and to self-position within the eye compared to single flexible footplates. This explains why the particular "reticulated" geometry of the distal region in the sense detailed above fully contributes to the disclosure and its advantages.

The phakic intraocular lens comprises, in some embodiments, at least two diametrically opposed flexible haptics endowed with such (reticulated) distal regions. Such combination of two flexible haptics improved the stability of the phakic intraocular lens in normal use in an eye. The phakic intraocular lens according to embodiments of the disclosure can nevertheless comprise a single flexible haptic as claimed, alone or in combination with any other haptic structure known by a man skilled in the art. For example, in the framework of the present disclosure, it can be considered a (rotationally asymmetric) phakic intraocular lens comprising a single flexible haptic with a distal region as described above, and at least one, preferably diametrically opposed, elongated flexible footplate, preferably extending between the first and second diameters, both partially circumferentially around one of the support elements and radially outward relative to the central optical part, and comprising a proximal extremity preferably mounted on the proximal portion and a free distal extremity configured for laying into the ciliary sulcus.

The peripheral haptic part and the flexible haptics are made of, for example, a very flexible and very resistant material. They constitute a compromise between the need for stability and compliance with intraocular structures, and the need for rigidity, avoiding excessive exertion of force and trauma to delicate intraocular structures, many of which are complex and not visible during or prior to implantation. They are structured to ensure that the vault as described above does not result from a compression of the lens exerted on their edge by the eye internal anatomy. The "flexible" characteristic of the flexible haptic and/or of the elongated flexible footplates is preferentially induced by this material combined with the above described reticulated geometry and/or the low average thickness of the flexible haptic and/or of the elongated flexible footplates measured along the optical axis. The "rigid" characteristic of the dome is induced, on the one hand, by a thickness, measured in parallel to the optical axis, significantly larger, on average, of the peripheral haptic part than that of the flexible haptic, and/or on the other hand, of a flared and/or wide and/or thick shape of the support elements, and/or yet again on the other hand, of the rigidity and adaptability of the geometric technical characteristics of the dome to a broad range of patient eye anatomies. The use of the term "rigid" is less for the purpose of qualifying the dome than to compare it to the flexible haptic.

In some embodiments, the thickness of the peripheral haptic part is targeted to allow the phakic intraocular lens to reside at a particular distance from the anterior surface of a natural crystalline lens by virtue of selectively titrating the curvature of the anterior and/or the posterior surfaces such that the posterior surface mimics the (anterior) curvature of the specific natural crystalline lens.

In the framework of the present disclosure, an "optical axis" of an eye consists, for example, in a vector crossing the eye from one side to the other, directed by its anterior segment, comprising successively, the cornea, the iris and the lens, to its posterior segment, comprising especially the retina. For a phakic intraocular lens according to embodiments of the disclosure in an implantation position in an eye, the optical axis of the eye is directed from the anterior surface to the posterior surface and corresponds, for example, to the optical axis defined intrinsically with respect to the phakic intraocular lens. The term optical axis is presently and preferentially used in this document as the reference axis with respect to the eye and/or to the phakic intraocular lens.

In the framework of the present disclosure, an "anterior" (or respectively, "posterior") side and/or surface of part of an eye or an intraocular lens consists, for example, in a side and/or surface located upstream (or respectively, downstream) of the part of the eye or the intraocular lens relative to the vector defined by the optical axis. By way of example, in an eye, the iris is located anteriorly with respect to the lens; a posterior surface of the iris is therefore a part of the iris that is the closest to the lens. Likewise, when a first part of an eye or of an intraocular lens is anteriorly (or respectively, posteriorly) above a second part of an eye or an intraocular lens, it follows that this first part is located anteriorly (or respectively, posteriorly) with respect to this second part.

The aforementioned notions of anteriority, posteriority or even of an optical axis relative to parts of an eye and/or an intraocular lens are well known to person skilled in the art.

For example, the phakic intraocular lens according to embodiments of the present disclosure is configured to be positioned in the posterior chamber of an eye, so that its anterior surface is at least partially facing the iris of the eye and so that its posterior surface is at least partially facing the natural crystalline lens of the eye.

In the framework of the present disclosure, it is said that part of a phakic intraocular lens extends "radially outward" when it extends, for example, according to vectors perpendicular to the optical axis, directed from a point in common with the optical axis to points of a circle centered at this common point. Likewise, it is said that a part of a phakic intraocular lens extends "circumferentially" when it extends, for example, along at least an arc of a circle on a plane perpendicular to the optical axis and centered on an intersection point of the plane and the optical axis. These notions of radial and circumferential extensions refer to a system of polar coordinates in each plane perpendicular to the optical axis.

It is well known by a person skilled in the art that the adjective "distal" refers to a part of a portion of a body the furthest form a reference organ or from a trunk of a body, and that the adjective "proximal" refers to a portion of a part of a body the closest to a reference organ or to a trunk of a body. In the framework of the present document, these two definitions will apply to parts of an eye and/or a phakic intraocular lens according to embodiments of the disclosure, relative to a distance with respect to the referential optical axis. For example, a proximal portion of a phakic intraocular lens according to embodiments of the disclosure comprises a central optical part and/or a part of the phakic intraocular lens around a central part, and a distal portion of a phakic intraocular lens according to the disclosure comprises an external lateral edge of the phakic intraocular lens apt to reach part of an eye.

In the framework of the present disclosure, the use of the indefinite article "a", "an" or the definite article "the" to introduce an element does not exclude the presence of a plurality of these elements. In this document, the terms "first", "second", "third" and "fourth" are solely used to differentiate elements and do not imply any order in these elements.

In the framework of the present disclosure, the use of the verbs "comprise", "include", "involve" or any other variant, as well as their conjugational forms, cannot in any way exclude the presence of elements other than those mentioned.

According to a certain embodiment of the disclosure:
the first diameter is comprised between 12.5 and 14.5 mm; and/or
the second diameter is comprised between 11 and 12 mm.

As previously mentioned, these first and second diameters are measured perpendicularly to the optical axis.

In accordance with another embodiment, the first diameter is equivalent to 14 mm, when no radial and/or axial compression force is exerted on the phakic intraocular lens. In another embodiment, the second diameter is comprised between 11.2 and 11.3 mm, and in another embodiment, it is equivalent to 11.25 mm and it corresponds to a smaller sized ciliary sulcus, so that the rigid dome-shaped optical assembly has a size compatible with a broad range of patient eye anatomies. For example, the rigid dome-shaped optical assembly is small enough not to itself undergo compression in an eye. The difference between the first and the second diameter can be attributed to the (at least one) flexible haptic, and, for example, constitutes a flexible contribution that can be contracted to fill the gap between the second diameter of the rigid dome and the actual size of the patient's ciliary sulcus. So, the phakic intraocular lens according to embodiments of the disclosure is well adapted to the anatomy of any eye with a planned resultant vault, e.g. the above-mentioned distance, not being reliant on a compression of the flexible haptics of the phakic intraocular lens.

According to certain embodiments of the disclosure, a smooth posterior surface of the dome is substantially concave, for example concave and/or a radius of curvature of the smooth posterior surface of the dome is comprised between 8 and 10 mm, and equivalent to 9 mm in another embodiment.

Advantageously, the radius of curvature selected in this way allows the central optical part and the peripheral haptic part:
to form a dome, the posterior surface of which is more curved than the anterior surface of a lens, and/or such that a diameter of an anterior surface of the lens is smaller than this radius of curvature;
and consequently, to be essentially anteriorly above this anterior surface.

It is pointed out that the curvature and radius of curvature are well defined because the posterior surface of the dome is smooth and then at least regular in a mathematical analytic sense. For example, the posterior surface of the junction between the peripheral haptic part and the central optical part does not comprise any irregularity or angular point.

In some embodiments, this radius of curvature is smaller than the radius of curvature of an anterior surface of the natural crystalline lens of an eye. In other embodiments, this radius of curvature consists in the smallest average radius of curvature of an anterior surface of a natural crystalline lens of an eye. The radii of curvature of the anterior and posterior surfaces of the phakic intraocular lens are also optimized regarding the targeted dioptric power, and in such a way that the central thickness of the central optical part is kept substantially constant across a whole diopter range. Moreover, the clear optic of the phakic intraocular lens is well defined.

In some embodiments, the central optical surface is substantially convex in an anterior way and/or substantially planar and/or essentially perpendicular to the optical axis. This allows to deliver a vault without the need for compression and therefore flexing of the phakic intraocular lens anteriorly.

In some embodiments, the distal region comprises between 3 and 11, between 4 and 8 in some embodiments, elongated flexible footplates. According to a certain embodiment of the disclosure, the distal border is transverse to (all) the elongated flexible footplates and/or the distal region comprises a proximal border transverse to (all) the elongated flexible footplates, in such a way that the elongated flexible footplates are able to curve as a whole when axial and/or radial compression is exerted on the at least one flexible haptic, for example when the phakic intraocular lens is in normal use in an eye. In other words, the (reticulated) distal region comprises preferably at least two reticles transverse to the elongated flexible footplates, a first of these reticles consisting of a proximal border of the (reticulated) distal region and a second of these reticles consisting of the distal border.

For example, as each elongated flexible footplate is transverse (then, crossing and/or interlacing) both proximal and distal borders of the distal region, the elongated flexible footplates behave like a whole accordion grid system when axial and/or radial compression is exerted on the at least one flexible haptic. This allows the distal region to be both resistant and flexible under such compression. The flexible haptic according to this certain embodiment moreover allows to increase an angle of contact between the distal region and the ciliary sulcus, for example, when the size of the latter is small.

As a first alternative of this embodiment of the disclosure, the (reticulated) distal region consists of:
the elongated flexible footplates,
the proximal border, and the distal border,
bordering the cavities.

As a second alternative of this embodiment of the disclosure, the (reticulated) distal region comprises at least three reticles transverse to the elongated flexible footplates.

For example, according to this (or other) embodiment of the disclosure, each of elongated flexible footplates comprises a proximal extremity and a distal extremity, the proximal extremities of the elongated flexible footplates being joined by the proximal border, and the distal extremities of the elongated flexible footplates being joined by the distal border. For example, each elongated flexible footplate extends between the proximal and the distal borders of the distal region, providing the latter with a flexible and resistant accordion grid system curving as a whole when axial and/or radial compression is exerted on the flexible haptic. In addition, this makes the distal region easy to see and to manipulate during an implantation process in an eye.

According to a certain embodiment of the disclosure, the distal border extends both circumferentially and radially outward relative to the central optical part. The distal border advantageously proposes a large contact surface in a ciliary sulcus and the flexible haptic then offer better laying into a ciliary sulcus and greater stability both radially and in rotation.

According to another certain embodiment of the disclosure, the distal border comprises smooth ripples arranged to smoothly hook into a ciliary sulcus when the phakic intraocular lens is in normal use in an eye. Advantageously, the ripples facilitate a smooth hooking of the distal border into a ciliary sulcus. The ripples, for example, give a role of a pin to this distal border to lay and stabilize more easily into a ciliary sulcus. These ripples are preferably polished so that their contours are smooth and cannot irritate the ciliary sulcus or other sections of the eye anatomy. In some embodiments, the ripples follow a shape of the distal extremities of the elongated flexible footplates.

According to a certain embodiment of the disclosure, the elongated flexible footplates are configured for extending substantially along a plane whose normal vector forms an angle comprised between −15° and 15° with the optical axis. In some embodiments, the proximal region of the flexible haptic extends, for example, posteriorly essentially in parallel to one of the support elements whereas the distal region is not necessarily parallel to the proximal region, and this given a common border region in which the flexible haptic is mainly apt to curve, so as to change the orientation of the proximal region with respect to the distal region. An angle formed between the distal region and a perpendicular line to the optical axis is substantially arbitrary, although preferably corresponding with the above mentioned angle and then comprised between −15° and 15°, for example, in implantation position in an eye, so as to allow an orientation of the distal region that is adequate to lay into a ciliary sulcus. Optionally, the proximal and distal regions form another angle less than 5 in absolute value when the phakic intraocular lens is in production and has not yet been implanted in an eye, so that the insertion of the flexible haptic under the iris of a patient is facilitated.

According to an optional variation of the previous embodiment of the disclosure, the area of the cavities measured in the plane, for example, is at least twice greater than the area of the elongated flexible footplates measured in the plane. In other words, on this plane, the ratio of areas empty of solid matter of the (reticulated) distal region with respect to the areas full of solid matter of the elongated flexible footplates is greater than two. In some embodiments, the area of the cavities measured in the plane is at least twice, and four times in some embodiments, greater than the area of all the reticles of the (reticulated) distal region (those comprising the elongated flexible footplates) measured in the plane. For example, the reticles are then particularly thin and flexible.

In some embodiments, the distal region of the flexible haptic has a substantially constant thickness, measured along the optical axis.

According to a certain embodiment of the disclosure, and as described above, the proximal region extends radially outward and posteriorly relative to the central optical part, between two of the support elements. The flexible haptic can comprise material folds, for example in a common border region of the distal and proximal regions, arranged to facilitate a fold in material, so that it curves more or less sharply when axial and/or radial pressure is exerted.

Optionally, the flexible haptic comprises a lateral recess in its proximal region, which is apt to allow the latter to operate as a hinge between the flexible haptic and the proximal portion of the peripheral haptic part. In this way, the flexible haptic is more flexible, solid and smooth at its proximal region. Advantageously, the lateral recess also plays a role of a failsafe mechanism to prevent excessive force being transmitted from the flexible haptic to the central optical part. It controls a force applied by the flexible haptic to provide an adapted fixation into a ciliary sulcus and to prevent an erosion of delicate intraocular tissues.

Alternatively and/or in combination, and according various embodiments of the disclosure, the proximal region comprises a plurality of elongated flexible footplates that:
  extend at least partially radially outward and posteriorly relative to the central optical part, and
  border cavities, preferably open cavities, extending between the anterior and posterior surfaces.

These (open) cavities preferably constitute spaces empty of solid matter.

According to embodiments of the disclosure, the proximal region is at least locally reticulated, for example, and globally reticulated in some embodiments, similarly to the (reticulated) distal region. This provides the whole flexible haptic with an improved flexibility on both proximal and distal regions, with a better adaptability of the phakic intraocular lens to an arbitrary eye anatomy.

According to a certain embodiment of the disclosure, the proximal region has a reticulated geometry analog to the distal region according to any of the previous embodiments of the disclosure.

In some embodiments, the distal region and the proximal region according to this very preferred embodiment of the disclosure share a common connecting border (consisting of a reticle) transverse to the elongated flexible footplates of both distal and proximal regions, in such a way that the elongated flexible footplates of the proximal region are able to curve as a whole when axial and/or radial compression is exerted on the flexible haptic. This common connecting border extends, for example, substantially circumferentially around the central optical part, and has a shape of an arc of a circle of the second diameter.

In this case, the common connecting border is a common reticle to both distal and proximal regions of the flexible haptic, extending transversally to (and then, crossing and/or interlacing) the elongated flexible footplates of these regions.

Each of the elongated flexible footplates of the distal and proximal regions have preferably a proximal extremity and a distal extremity. In some embodiments, the common connecting border joins the distal extremities of the elongated flexible footplates of the proximal region, and the proximal extremities of the elongated flexible footplates of the distal region. In a specific embodiment of the disclosure, the elongated flexible footplates of the proximal region extend distally in the elongated flexible footplates of the distal region.

Each of the elongated flexible footplates of the proximal region extend preferably distally between the peripheral haptic part, more preferably its proximal portion, and this common connecting border. Alternatively, the elongated flexible footplates of the proximal region can extend between another intermediary reticle of the proximal region which is transverse to the elongated flexible footplates of the proximal region and the common connecting border, this another intermediary reticle then connecting the proximal extremities of the elongated flexible footplates of the proximal region. Otherwise, optionally, the proximal region comprises a distal reticulated part comprising the elongated flexible footplates of the proximal region, and a proximal non reticulated part on which is mounted the distal reticulated part, and itself preferably mounted on the proximal portion of the peripheral haptic part.

The common connecting border can optionally be provided with at least a recess for improving flexibility between the distal and the proximal regions and allowing it to act as a hinge between these regions.

In some embodiments, the elongated flexible footplates of the proximal region are oriented and substantially parallel to a first direction. In other embodiments, the elongated flexible footplates of the distal region are oriented and substantially parallel to a second direction. This allows advantageously to manufacture more easily the flexible haptic. Moreover, this particular orientation and design of the elongated flexible footplates improve the maneuverability of the distal and/or proximal regions, and/or their flexibility as a whole accordion grid. In some embodiments, these first and second directions are transverse and forms a smaller angle between them comprises between 80° and 140°, and between 100° and 120° in some embodiments.

According to an embodiment of the disclosure, the phakic intraocular lens comprises a first, a second, a third and a fourth support elements, for example, inscribed within a cylinder elongated along the optical axis, centered in the central optical part, with a diameter equal to the second diameter, the first and second support elements extending in a diametrically opposed way on either side of the optical axis, the third and fourth support elements extending in a diametrically opposed way on either side of the optical axis. According to another embodiment of the disclosure, the phakic intraocular lens comprises two flexible haptic according the disclosure, which are, for example, oriented and diametrically opposed. Other numbers of flexible haptics (for example, four flexibles haptics rotationally symmetrically oriented) are not excluded from the scope of the disclosure.

Advantageously, this arrangement of the support elements and the flexible haptic provides the phakic intraocular lens according to embodiments of the disclosure with a greater stability both axially and radially as well as in rotation. For example, the vault as predetermined space between the phakic intraocular lens and the natural crystalline lens is not dependent upon a lateral force exerted through the whole phakic intraocular lens body exerting compression. If such a lateral force occurs this phakic intraocular lens design absorbs it within the flexible haptic such that the rigid optical assembly remains unaffected by any such compression.

The extension of a pair of support elements on either side of the optical axis, in a diametrically opposed way, can be assimilated to a collection of planar central symmetries of points of this pair of support elements. In some embodiments, the extension is not necessarily realized along a line or a diameter, but along a smooth curve extending symmetrically on both sides of the optical axis.

In some embodiments, the first, second, third and fourth support elements are radially oriented to the exterior relative to the central optical part, symmetrically according to the diagonals of a planar rectangle intersecting on the optical axis. The vertices of the first plane rectangle are preferentially arranged on the cylinder. The ratios of the largest side of the planar rectangle with the smallest side of the planar rectangle are, for example, comprised between 1 and 1.5.

In some embodiments, the two flexible haptic have an orientation such that there are respectively image one of the other by a rotation of 180° of the phakic intraocular lens around the optical axis. This is very advantageous and critical for the case of a lens comprising a curvature irregularity to correct astigmatism, for example, in the case of a phakic toric intraocular lens. In this case, it is often necessary to preoperatively rotate the phakic intraocular lens to position it in a proper axis. The design and the rotational symmetry of the flexible haptics facilitate advantageously such rotation maneuver at the time of surgery.

More generally, it is a certain embodiment that the phakic intraocular lens is shape invariant under a rotation of 180° around the optical axis. For example, the claimed shape invariance comprises, for example, a rotational symmetry of both haptic structures: the preferred and specific four support elements and the two flexible haptics.

According to a certain embodiment of the disclosure, the phakic intraocular lens comprises a flexible and biocompatible material comprising between 20 and 45% water, a Young module of which being less than 1 GPa.

In some embodiments, this flexible and biocompatible material comprises 36 to 38% water. In some of these embodiments or others, this material has a Young module comprised between 0.25 and 0.75 GPa, between 0.4 and 0.6 GPa in some embodiments, and is 0.5 GPa in other embodiments.

This flexible and biocompatible material is more flexible, for example, than a material usually used in capsular intraocular lens design. It comprises, for example, a highly hydrophilic covalently attached coating for very low surface friction, negative zeta potential, soft touchiness and anti-fouling features.

In some embodiments, the phakic intraocular lens is extensively polished on each of its external surfaces, for example, on the anterior, posterior and lateral surfaces, in order to make round haptic edges and intraocular lens contour after milling. This allows to avoid one side or sharp edge of a flexible haptic, of the peripheral haptic part or the central optical part, to be able to irritate the tissues of a posterior chamber of a patient's eye when a phakic intraocular lens is in an implantation position or during the surgery.

Moreover, according to a certain embodiment of the disclosure, the phakic intraocular lens comprises a through bore extending between the anterior and posterior surfaces and arranged to allow a fluid flow.

In some embodiments, the fluid flow is a flow of a liquid between the anterior and posterior chambers of an eye when the phakic intraocular lens is in normal use in an eye. This bore advantageously allows to prevent a second and artificial posterior chamber to be created with a resultant limitation of a fluid flow between a space anterior and a space posterior to the phakic lens regardless of the actual size of either of these spaces. It makes possible to guarantee a full and permanent fluid communication between the anterior and posterior chambers of the eye. In some embodiments, the through bore is located in a center of the central optical part, more preferably at least partially at its intersection with the optical axis.

The disclosure advantageously allows a choice of central optical part lens that is best adapted to a defect in vision that is to be corrected in a patient.

For example, according to an embodiment of the disclosure, the central optical part lens consists in a monofocal lens that allows at least one correction from among: a correction of myopia, a correction of hypermetropia, a correction of presbyopia and a correction of corneal astigmatism. According to a certain embodiment of the disclosure, the lens consists in a lens at extended refractive or diffractive depth of focus, and to treat, for example, presbyopia.

DESCRIPTION OF THE DRAWINGS

The foregoing aspects and many of the attendant advantages of the claimed subject matter will become more readily appreciated as the same become better understood by reference to the following detailed description, when taken in conjunction with the accompanying drawings, wherein:

FIG. 4A illustrates a simplified three-dimensional representation of the side and partially of the posterior surface of a posterior chamber phakic intraocular lens according to an embodiment of the disclosure;

FIG. 4B illustrates a simplified three-dimensional representation of the anterior surface of the posterior chamber phakic intraocular lens illustrated in FIG. 4A;

Each one of FIGS. 7A-C illustrates an enlarged view of a flexible haptic of a posterior chamber phakic intraocular lens according to embodiments of the disclosure.

Figure 1A:
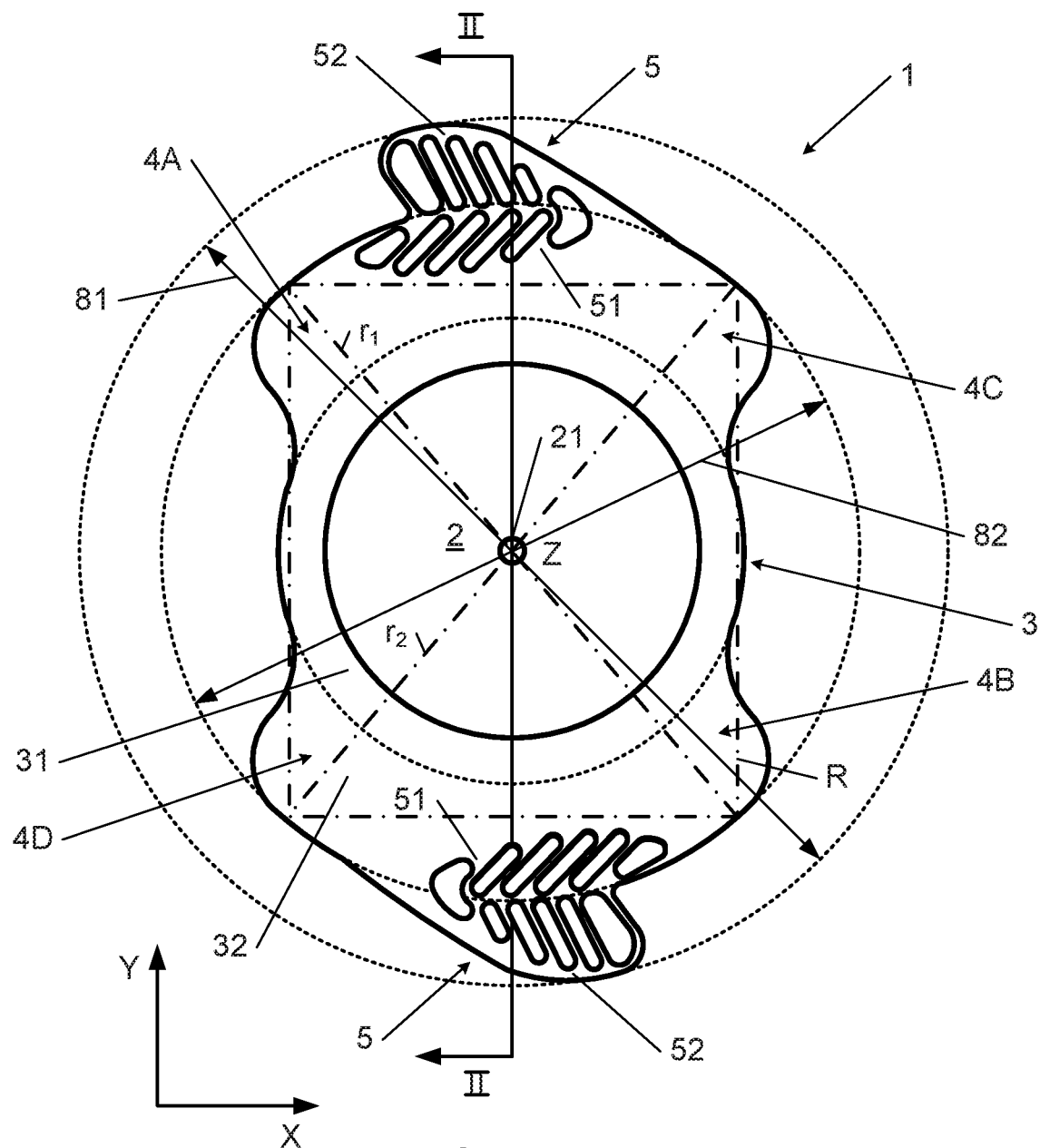
FIG. 1A illustrates a first simplified planar representation of the top of a posterior chamber phakic intraocular lens according to an embodiment of the disclosure, provided with abstract geometric guiding marks.

The drawings in the figures are not scaled. Generally, similar elements are assigned by similar references in the figures. In the framework of the present disclosure, identical or analogous elements may have the same references. Moreover, the presence of reference numbers in the drawings cannot be considered to be limiting.

DETAILED DESCRIPTION

The detailed description set forth below in connection with the appended drawings is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

The geometric elements and/or measures designated by references 81, 82, 83, 83', 89A, 89B, X, Y, Z, K, d, P, R, α, r1 and r2 are represented in some of the figures as an illustration in order to quantify and/or visualize technical properties of embodiments of the disclosure. These geometric elements are substantially abstract and do not correspond to concrete material objects.

Similarly, various dotted lines are represented in FIGS. 1A-B, 4A-B and 7A-C for the only purpose of showing some limits of regions and/or parts of the phakic intraocular lens according to some embodiments of the disclosure. These lines do not materially exist.

The present disclosure provides an example of a posterior chamber phakic intraocular lens 1 that is both adapted to any eye anatomy and postoperatively stable in an implantation position in an eye 9, both axially along the optical axis Z, radially and in rotation in a plane perpendicular to the optical axis Z based on the vectors X and Y. The optical axis Z is directed from an anterior surface 11 of the phakic intraocular lens 1 to a posterior surface 12 of the phakic intraocular lens 1.

As it is illustrated in the figures, the phakic intraocular lens 1 comprises a central optical part 2 extending radially relative to the optical axis Z, and in an essentially planar and/or substantially convex way, with a diameter comprised between 5.5 and 6.5 mm, preferentially equivalent to 6 mm. It comprises a through bore 21 elongated along the optical axis Z and extending between anterior 11 and posterior 12 surfaces, so as to allow fluid communication between these surfaces.

Figure 1B:
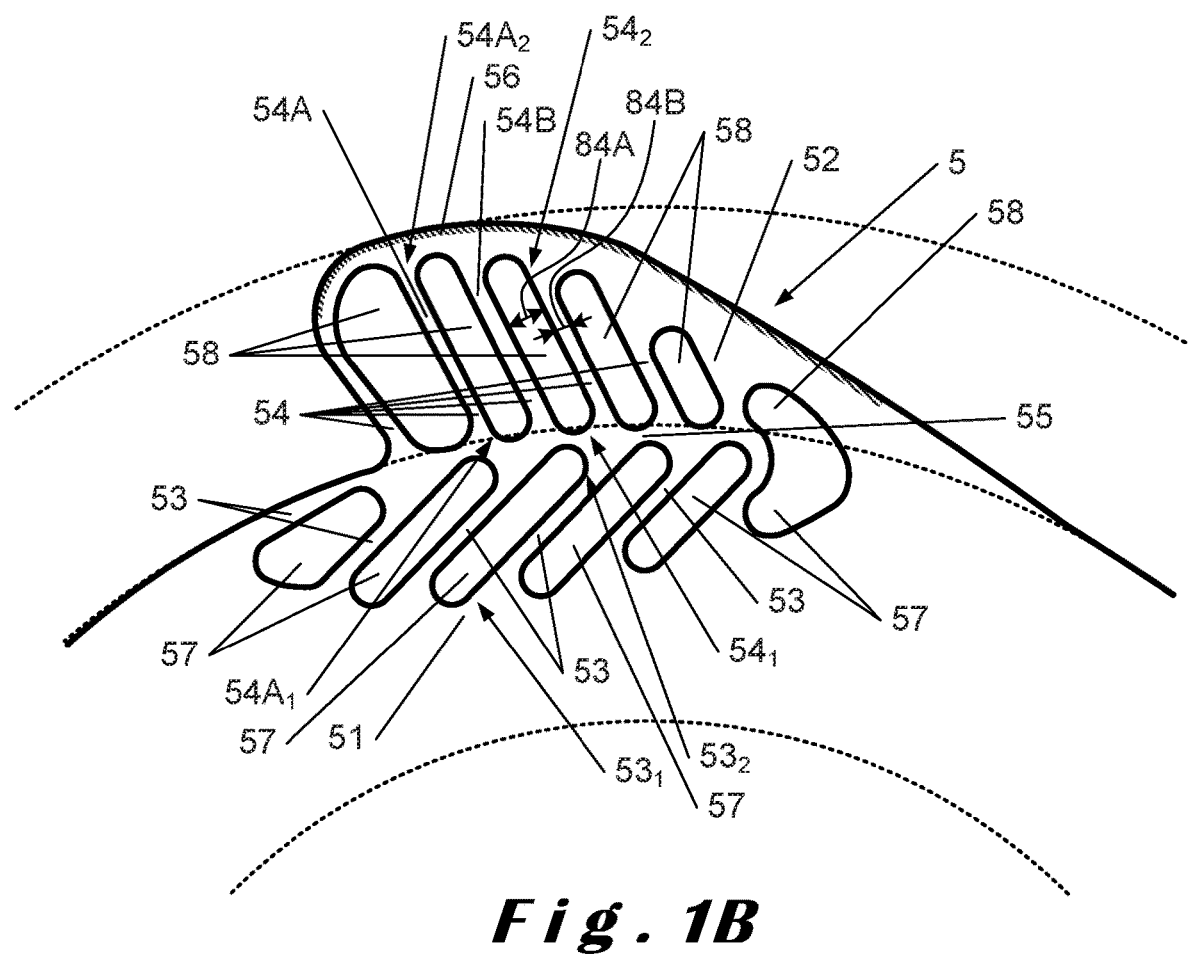
FIG. 1B illustrates an enlarged view of a flexible haptic of the posterior chamber phakic intraocular lens represented in FIG. 1A.

As it is illustrated in FIGS. 1A and 1B, the phakic intraocular lens 1 comprises, for example, a peripheral haptic part 3 extending radially outward relative to the central optical part 2, and comprising:

a proximal portion 31 extending circumferentially and substantially symmetrically around and from the central optical part 2;

a distal portion 32 prolonging at least partially in a radial way, the proximal portion 31 and comprising a plurality of support elements 4A-D extending radially outward along the diagonals r1 and r2 of a planar rectangle R perpendicular to the optical axis Z, and also extending posteriorly relative to the central optical part 2;

so that the central optical parts 2 and peripheral haptic parts 3 form a dome K supported by broad feet consisting in support elements 4A-D.

Figure 2:
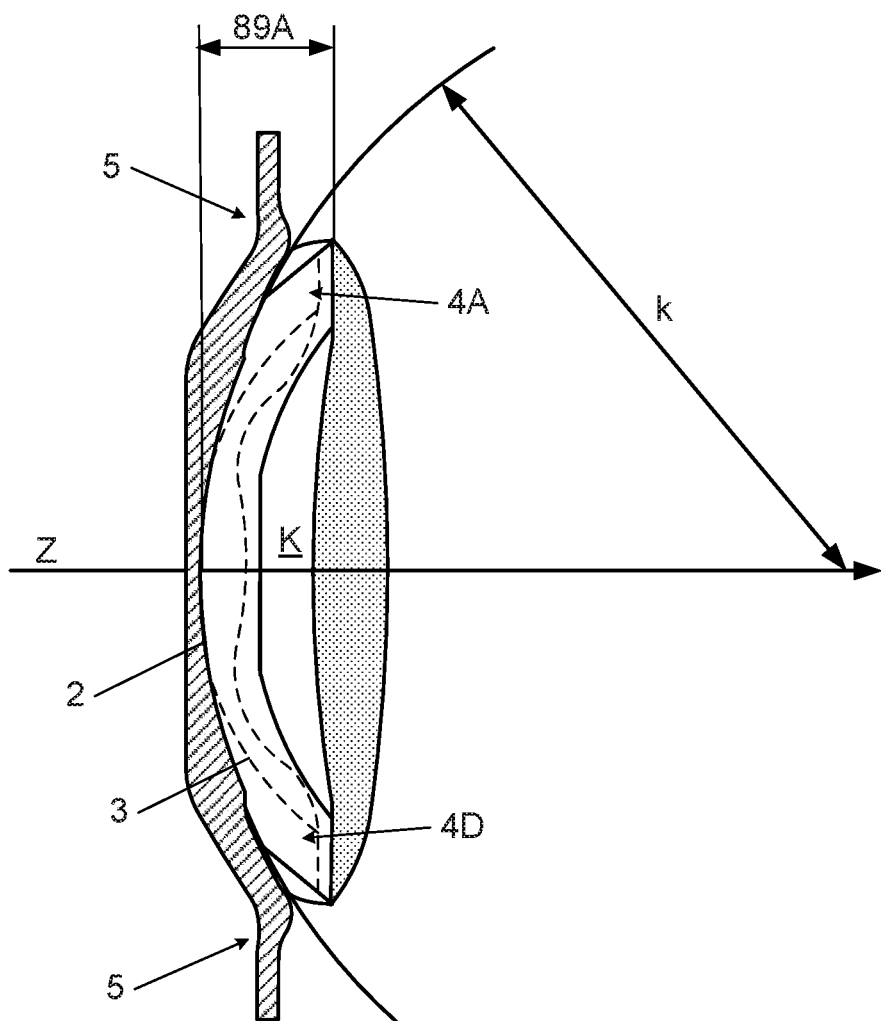
FIG. 2 illustrates a second simplified planar representation of a side of the posterior chamber phakic intraocular lens represented in FIG. 1A.

Dome K is represented in FIG. 2. A sufficient wall thickness confers rigidity to the dome K so that it is resistant under axial and/or radial compression. A posterior surface of the dome K is curved and its preferential radius of curvature k is approximately 9 mm, so that the dome K can be inscribed into a sphere with radius k as illustrated in FIG. 2.

A height 89A of the dome K, measured along the optical axis Z, and as illustrated in FIG. 2, and the "inherent vault", constitute a height of a vault inherent to the phakic intraocular lens 1. It accepts a preferential value comprised between 1.5 and 2.2 mm, more preferably between 1.7 and 2 mm, even more preferably it is 1.87 mm. The width of a base of dome K corresponds typically to a second diameter 82 of the central optical 2 and peripheral haptic 3 parts. This second diameter 82 corresponds approximately to 11.25 mm. The "top" portion of the dome K corresponds substantially to the central optical part 2 and the proximal portion 31 of the peripheral haptic part 3, and extends with a diameter corresponding approximately to 7 mm.

Figure 3:
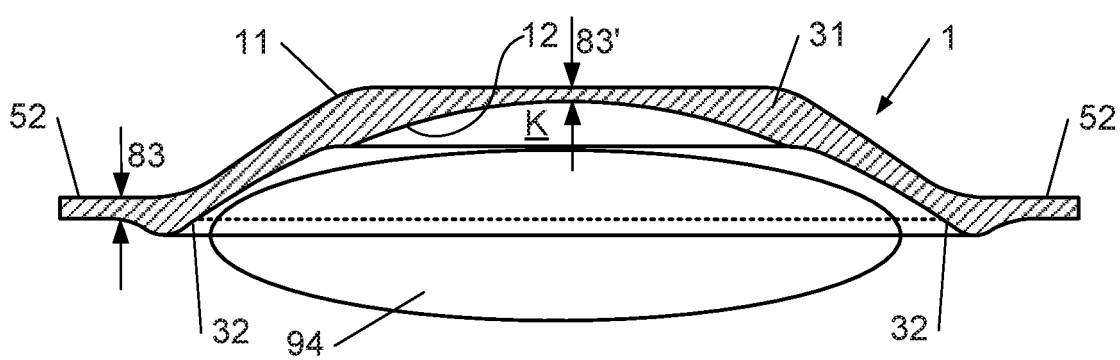
FIG. 3 illustrates a third simplified planar representation of a front of the posterior chamber phakic intraocular lens represented in FIG. 1A.

As presented in detail in the summary of the disclosure, these values are selected so that the assembly composed of the central optical 2 and peripheral haptic 3 parts are apt to constitute a sufficiently rigid and sufficiently broad structure to surround and sit anteriorly above a natural crystalline lens 94 of an eye, as diagrammed in FIG. 3, and thereby to be implanted in a very broad range of anatomies of eye posterior chambers, while being stable in parallel to the optical axis Z.

As illustrated in FIGS. 1A and 1B, the phakic intraocular lens 1 also comprises at least one, more precisely two, flexible haptics 5, each one extending radially outward with respect to the central optical part 2 between two support elements 4A-D, and radially beyond the peripheral haptic 3 so as to inscribe in a cylinder of a first diameter 81 with a value comprised preferentially between 13.5 and 14.5 mm, more preferably corresponding to 14 mm, in a non-implanted state, without axial or radial compression exerted on the phakic intraocular lens 1.

These two flexible haptics 5, more specifically their distal border 56 for example, are configured for stabilizing the phakic intraocular lens 1 into a ciliary sulcus when it is in normal use in an eye. As it is detailed in the summary of the disclosure, these flexible haptics 5 allow to compensate for the size variations of a ciliary sulcus with the phakic intraocular lens 1 is in an implantation position. They also act as lateral anchors for stabilizing the phakic intraocular lens 1 in rotation in a plane perpendicular to the optical axis Z.

As showed in FIGS. 1A-B and 4A-B, each of the flexible haptic 5 consists of:
  a (at least locally) reticulated proximal region 51 mounted on the peripheral haptic part 3, preferentially on its proximal portion 31;
  and a reticulated distal region 52 mounted on the proximal region 51.

The proximal region 51 extends typically radially outward and posteriorly relative to the central optical part 2, between two of the support elements 4A-D. The distal region 52 is mounted on a common connecting border 55 extending substantially along an arc of circle of the second diameter 82. This common connecting border 55 is a proximal border of the distal region 52 and a distal border of the proximal region 51. The distal region 52 comprises a distal border 56 comprising smooth ripples 56A for laying (and/or hooking and/or stabilizing itself) into a ciliary sulcus when the phakic intraocular lens 1 is in normal use in an eye.

As more clearly showed in FIGS. 4A-B, each of the flexible haptic 5 has a form of a curved perforated tree leaf with two lobes corresponding respectively to the proximal 51 and distal 52 regions. The above-mentioned term "perforated" is linked to the (at least locally) "reticulated" technical characteristic of the proximal 51 and distal 52 regions. As a consequence of these characteristics these regions comprises a plurality of interlacing reticles forming a net. This geometry is very particular and very specific for an haptic geometry. It is fully part of the disclosure. Its main advantage is to provide the phakic intraocular lens 1 with very flexible haptics that is sufficiently connected to the peripheral haptic part 3 to avoid any flipping of the flexible haptics 5 during an implantation process of the phakic intraocular lens 1. Moreover, such a flexible haptic 5 is easier to see into the eye during this process, which is very important for handling position adjustment of the phakic intraocular lens 1 into an eye. In brief, this reticulated geometry for the flexible haptics 5 is specifically design for improving maneuverability of the phakic intraocular lens 1 into an eye, while allowing for its rotational stability as described above.

The reticles of the (at least locally) reticulated proximal 51 and distal 52 regions are now specifically described in view of FIG. 1B. The reticles of the proximal region 51 comprise oriented elongated flexible footplates 53 extending substantially in parallel from the peripheral haptic part 3 to the common connecting border in a first direction. The reticles of the distal region 52 comprise oriented elongated flexible footplates 54 extending substantially in parallel from the common connecting border 55 to the distal border 56 of the distal region 52 in a second direction transverse to the first direction, preferentially with a (smallest) angle comprises between 80 and 120° between these two directions. The elongated flexible footplates 53, 54 extend then at least partially radially outward relative to the central optical part 2. They are preferentially similar elongated thin reticles with a width 84B measured transversally to the second direction comprised between 0.05 and 0.20 mm, preferably corresponding substantially to the value 0.10 mm. Each elongated flexible footplates 53 (respectively 54) comprises a proximal $53_1$ (respectively $54_1$) and a distal $53_2$ (respectively $54_2$) extremities. The common connecting border 55 constitutes a reticle of both proximal 51 and distal 52 regions transverse to the elongated flexible footplates 53, 54 and joining together the distal $53_2$ extremities of the elongated flexible footplates 53 and the proximal $54_1$ extremities of the elongated flexible footplates 54. The distal border 56 constitutes a reticle of the distal region 52 transverse to the elongated flexible footplates 54 and joining together the distal $54_2$ extremities of the elongated flexible footplates 54. The smooth ripples 56A of the distal border 56 follow preferentially a joining shape of distal extremities $54_2$ extremities of the elongated flexible footplates 54 as it is illustrated in FIGS. 4A-B. Two elongated flexible footplates 54A and 54B extend substantially between the second 82 and the first 81 diameters. In other words, the phakic intraocular lens 1 comprises elongated flexible footplates 54A-B with distal extremities 54A-$B_2$ for laying into a ciliary sulcus when it is in normal use in an eye. These elongated flexible footplates 54A-B are joined advantageously into a reticulated flexible haptic 5 as described above which allows to improve its flexibility and its maneuverability. The proximal $53_1$ extremities of the elongated flexible footplates 53 are preferably joined together on the proximal portion 31 of the peripheral haptic part 3. As a consequence, the elongated flexible footplates 53, 54 are joined and work as a whole flexible accordion grid curving and/or moving under axial and/or radial compression exerted on the flexible haptics 5 when the phakic intraocular lens 1 is in an implanted position. In some embodiments, the proximal 51 and distal 52 regions only comprise reticles as a solid matter constituting them. There are then open cavities (or, equivalently, spaces empty of such solid matter) extending between the anterior 11 and posterior 12 surfaces and being bordered by the reticles. These cavities are denoted by the reference numbers 57 and 58 respectively for the proximal 51 and distal 52 regions. They are typically oriented and elongated similarly to the elongated flexible footplates 53, 54. A width 84A of the cavities 58 measured transversally to the second direction is comprised between 0.10 and 0.50 mm, preferably between 0.20 and 0.30 mm, more preferably it corresponds substantially to the value 0.26 mm. As a consequence, the distal region 52 is preferably much emptier of the solid matter that full of the solid matter. The same can apply for the proximal region 51.

Figure 7A:
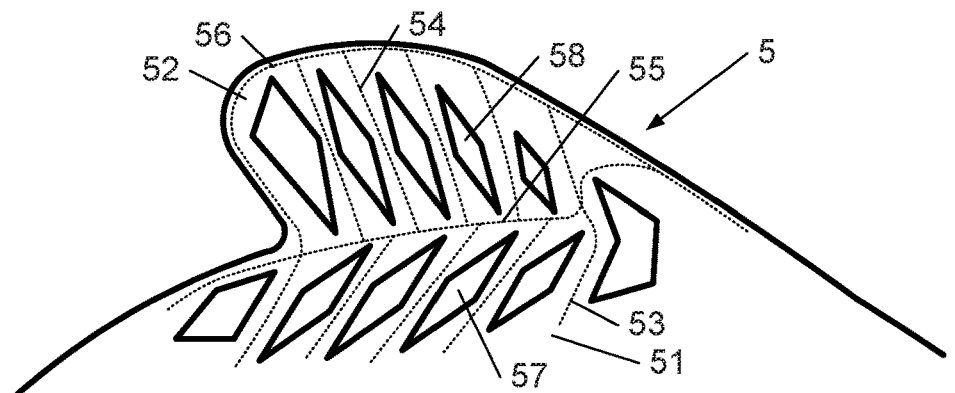
Figure 7B:
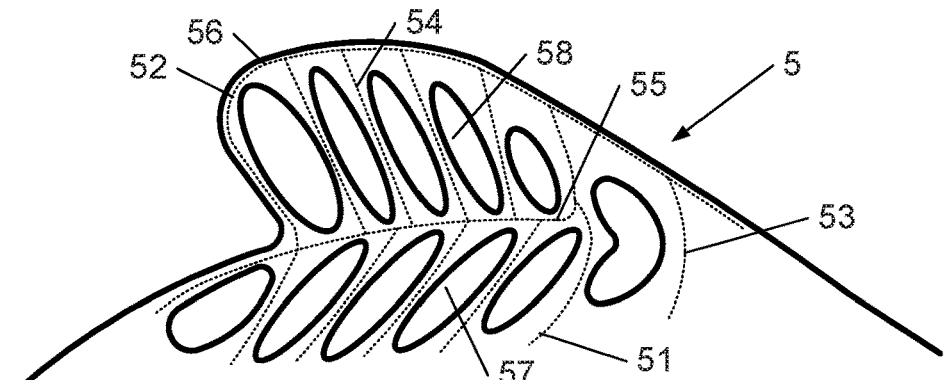
Figure 7C:
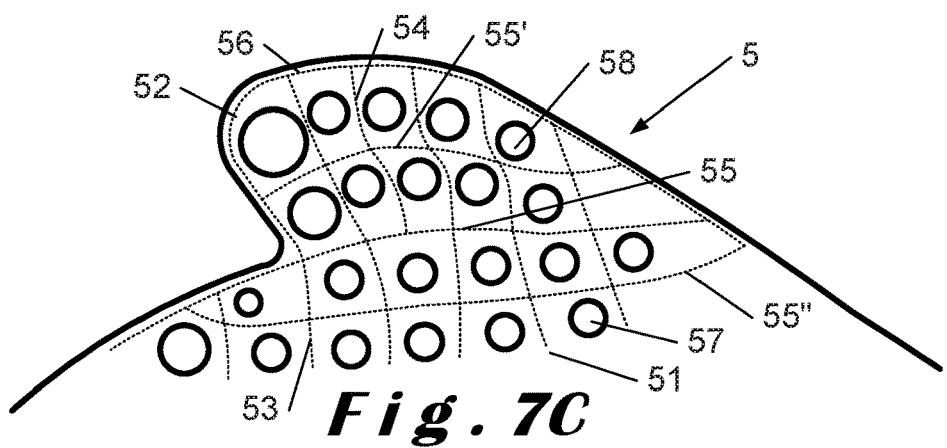

The number of reticles and their arrangement was described previously in view of FIGS. 1A-B and 4A-B. For example, in this case, the open cavities 57, 58 have oblong shapes. Nevertheless, in the framework of the disclosure, it is possible to consider an arrangement of reticles providing open cavities 57, 58 with other shapes such as rhombus, ellipses or circles as it is illustrated in a non limitative way in FIGS. 7A-C. The dotted lines on these figures represent extension directions of the reticles. In FIG. 7C, it is illustrated a proximal 51 (respectively distal 52) region comprising an additional intermediary reticle 55" (respectively 55') transverse to the elongated flexible footplates 53 (respectively 54).

The (at least locally) reticulated geometry of the flexible haptics 5 allows advantageously them to be both strongly resistant and flexible. It also confers great solidity and resistance to the connections between the distal 52 and the proximal 51 regions, as well as between the proximal region 51 and the proximal portion 31 of the peripheral haptic part 3. The flexible haptics 5 are constituted from a flexible and resistant material comprising preferably 38% water, which combined with their geometry contributes to their strong resistance and flexibility.

As illustrated in FIGS. 3 and 4A, a thickness 83 of the distal region 52 measured along the optical axis Z is preferably substantially constant, and comprised between 0.10 and 0.40 mm, more preferably between 0.15 and 0.35 mm, and greater than a thickness 83' of the central optical part 2. Optionally, it corresponds either to 20 or to 30 mm. Nevertheless, it is possible to consider a distal region 82 whose thickness 83 decreases substantially from the common connecting border 55 to the distal border 56 in order to be inserted and/or to stabilize more easily into a ciliary sulcus of an eye.

Figure 6:
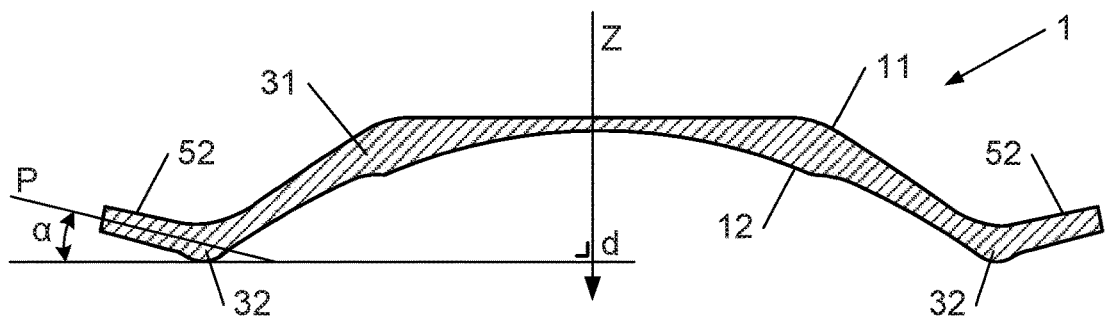
FIG. 6 illustrates a simplified planar representation of the side of a posterior chamber phakic intraocular lens according to an embodiment of the disclosure.

The distal region 52 is designed for folding and/or curving when compression is exerted axially and/or radially on the phakic intraocular lens 1, in such a way that an adjustable angle α between a line d perpendicular to the optical axis Z and a plane P of extension of the distal region 52 is preferentially comprised between −15° and 15°, as illustrated in FIG. 6.

The two flexible haptics 5 as represented in FIGS. 1A-B and 4A-B are disposed and designed to provide the phakic intraocular lens 1 with an "aerodynamic" rotationally symmetric shape. In some embodiments, the distal border 56 is extends circumferentially and radially outward with respect to the central optical part 2. Moreover, the shape of the whole phakic intraocular lens 1 is invariant under a rotation of 180° around the optical axis Z. This shape of the phakic intraocular lens 1, and more particularly of the flexible haptics 5, is advantageous for handling axis adjustment in rotation after having implanted the phakic intraocular lens 1 in an eye. In fact, it is important to avoid a flipping of the flexible haptics 5 or damages to intraocular tissues of the eye during such an axis adjustment, and the shape of the flexible haptics is particularly adapted for that.

Figure 5:
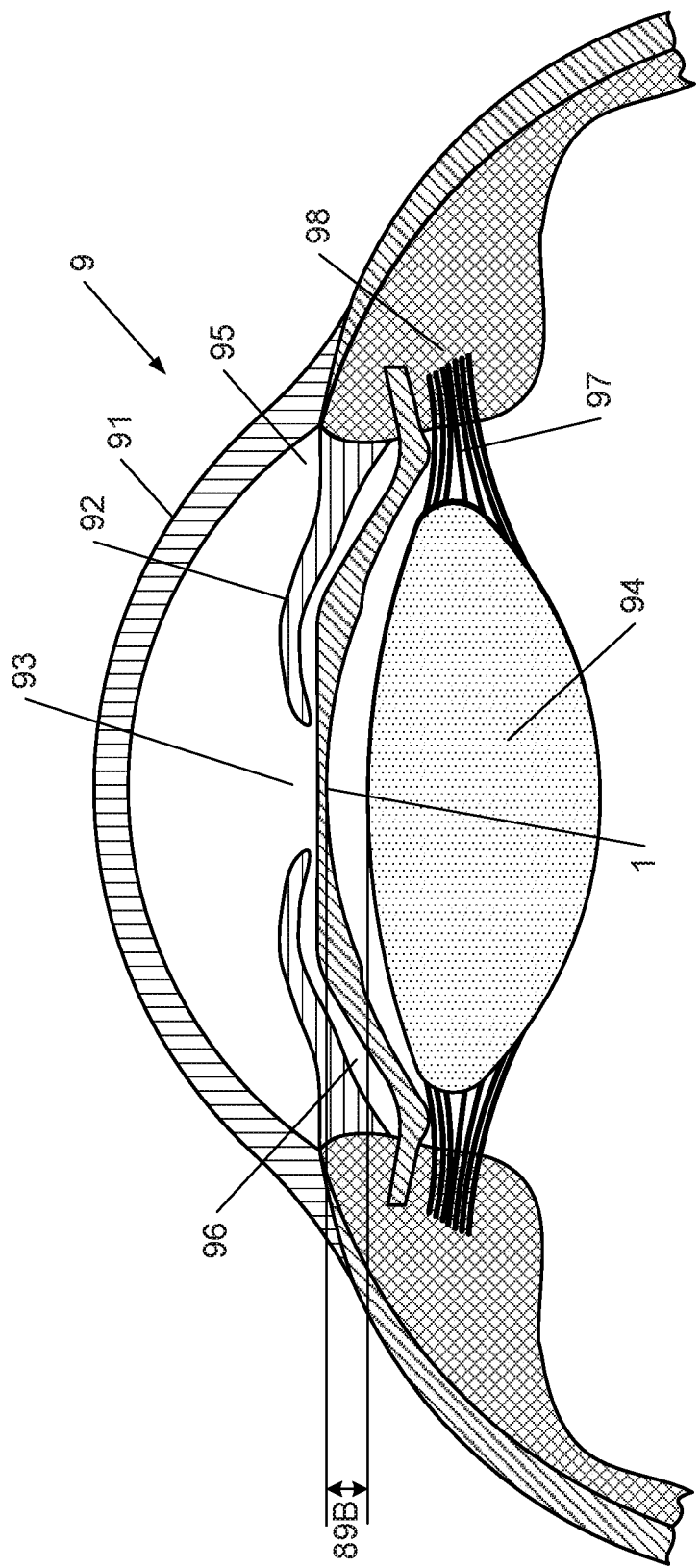
FIG. 5 illustrates a simplified cross-sectional view of part of an eye in which a posterior chamber phakic intraocular lens according to an embodiment of the disclosure has been fitted.

FIG. 5 illustrates a cross-section of an eye 9, in which a phakic intraocular lens 1 according to the present disclosure is implanted according to the disclosure. On this cross-section the following are represented: a cornea 91, an iris 92, a pupil 93, a lens 94, and anterior chamber 95, a posterior chamber 96, a ciliary zonule 97 and a ciliary sulcus 98 of the eye 9. The phakic intraocular lens 1 is placed in the posterior chamber 96. The support elements 4A-D of the peripheral haptic part 3 rest on the ciliary zonule 97 while the flexible haptics 5 are made to lay into the ciliary sulcus 98 as described and commented on in the summary of the disclosure. A distance of security 89B, referred to as the vault, between the lens 94 and the posterior surface of the phakic intraocular lens 1 measured along the optical axis Z is preferentially comprised and adjustable between 350 and 700 microns. The double structure of haptics 4A-D and 5 allow advantageously axial and radial stabilization and rotational stability of the phakic intraocular lens 1 in its implantation position. The distance of security 89B advantageously does not depend either on the eye sizing or on the compression in implanted state.

Figure 8:
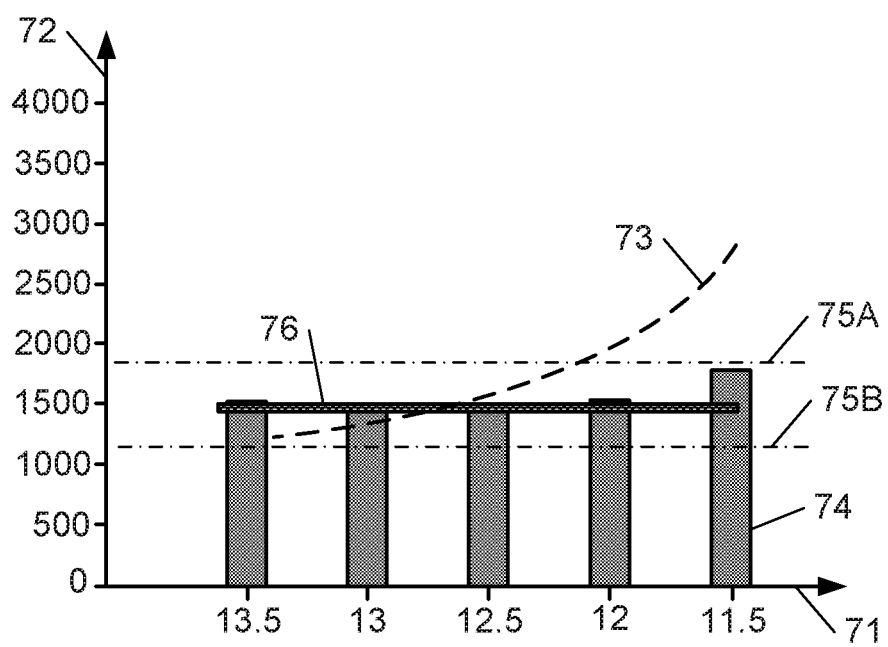
FIG. 8 illustrates a graphic representation of an axial position of a posterior chamber phakic intraocular lens according to an embodiment of the disclosure on the basis of a ciliary sulcus diameter.

FIG. 8 represents a graphic representation 74 of an axial position of a posterior chamber phakic intraocular lens according to the disclosure, indicated on the axis 72 and measured in microns on the basis of a mimicked ciliary sulcus diameter, indicated on axis 71 and measured in millimeters. A desirable equilibrium position is represented by a line 76 at 1500 microns measured on the axis 72, this value corresponding to an aforementioned distance 89B of 500 microns. An axially accepted margin of variation according to the optical axis Z around this equilibrium position 76 is of 350 microns. This margin is represented at its high and low limits by two dotted lines 75A and 75B respectively. The graph 74 shows that the axial displacements of the phakic intraocular lens 1 on the basis of the size of the ciliary sulcus vary very little and remain within the accepted values between lines 75A-B for a broad range of sizes of ciliary sulci comprised between 11.5 and 13.5 mm. The curve 73 illustrated by a dotted line represents a measurement trend of an average axial displacement of an average posterior chamber phakic intraocular lens according to the prior art and with a diameter of 12.6 mm. Comparison of chart 74 and the tendency curve 73 illustrates the performances and the improvements in terms of axial stability of the phakic intraocular lens 1 according to the disclosure.

In other words, the present disclosure relates to a posterior chamber phakic intraocular lens 1 comprising a central optical part 2, a peripheral haptic part 3 comprising a plurality of support elements 4A-D arranged to lie on a ciliary zonule of an eye, and at least one flexible haptic 5 comprising a reticulated distal region 52 arranged to lay into a ciliary sulcus of the eye.

The present disclosure was described in relation to the specific embodiments which have a value that is purely illustrative and should not be considered to be limiting. Generally speaking, it seems obvious for the person skilled in the art that the present disclosure is not limited to the examples illustrated and/or described above. The disclosure comprises each of the new characteristics described throughout the present document, as well as all their combinations.

The present disclosure was also described in relation to the advantageous technical development of a posterior chamber phakic intraocular lens both adapted to any eye anatomy and postoperatively stable in an implantation position in an eye, axially along the optical axis, and radially and in rotation in a plane perpendicular to the optical axis. As described previously, this phakic intraocular lens comprises at least one flexible haptic with a preferred reticulated geometry. The inventors also propose a very advantageous inclusion of this at least one flexible haptic in an (aphakic or phakic) intraocular lens. The inventors also propose to replace at least one known haptic of an intraocular lens by such claimed flexible haptic.

Another aim of the disclosure is to provide an (aphakic or phakic) intraocular lens stable in rotation in a plane perpendicular to the optical axis in implantation position in an eye and particularly easy to see and to maneuver during an implantation process in an eye.

For this purpose, the inventors propose an (aphakic or phakic) intraocular lens comprising:
- an anterior surface and a posterior surface;
- a central optical part comprising a lens, and extending radially relative to an optical axis directed from the anterior surface to the posterior surface;
- at least one flexible haptic 5 (in one piece) comprising:
  - a (reticulated and preferably distal) region 52 at least around the central optical part and comprising a plurality of elongated flexible footplates 54 that:
    - extend at least partially radially outward relative to the central optical part, and that
    - border (preferably open) cavities 58 that extend between the anterior and posterior surfaces;
- the region 52 also comprising a distal border 56
- connecting at least two of the elongated flexible footplates 54, and
- being configured for stabilizing the intraocular lens when it is in normal use in an eye.

The above mentioned reference numbers typically echo the shape of the flexible haptic 5 in FIG. 1B that can widely be adapted to a large class of (aphakic or phakic) intraocular lens. The whole set of embodiments of the flexible haptic 5 described and claimed for the phakic intraocular lens according to the disclosure and the advantages of these embodiments use apply mutatis mutandis to the present flexible haptic 5 and (aphakic or phakic) intraocular lens. For example, this flexible haptic 5 provide the (aphakic or phakic) intraocular lens with an improved stability in rotation in a plane perpendicular to the optical axis and an improved resistance under radial compression. This disclosure is more general than the claimed posterior chamber phakic intraocular lens, but the fact that claimed (reticulated) flexible haptic provides these advantageous effects by itself is fully part of the present disclosure. The claimed peripheral haptic part forming a dome is important for targeting a full stability of the claimed posterior chamber phakic intraocular lens, but it is not necessary for obtaining the technical effect of stability of a more general (aphakic or phakic) intraocular lens in rotation in a plane perpendicular to the optical axis and the other technical effect of having haptic particularly easy to see and to maneuver during an implantation process in an eye. Therefore, the inventors also propose the intraocular lens so without a peripheral haptic part forming a dome.

The term "reticulated" has to be interpreted as previously as having a geometry mimicking a net, the reticles of the region comprising at least the elongated flexible footplates and the distal border. As explained previously in the summary, the flexibility of the flexible haptic is at least partially due to the "reticulated" geometry and/or to the flexibility of the elongated flexible footplates. The region is particularly flexible so that it allows a postoperatively stable implantation of the intraocular lens in an eye independently of size variations of the implantation position. The distal border connects at least two of the elongated flexible footplates, one of them being preferably said a longest elongated flexible footplate, which provides at least locally the region with said "reticulated" structure and contributes to the one-piece structure retention of the region. As explained previously in the summary, it is practical to consider flexible footplates as reticles of a reticulated distal region of a one piece flexible haptic because this reticulated structure allows to use flexible footplates for stabilizing the intraocular lens while being very easy to see and to maneuver during an implantation process in an eye, and to self-position within the eye compared to single flexible footplates.

In some embodiments, the (aphakic or phakic) intraocular lens comprises at least two diametrically opposed flexible haptics endowed with such (reticulated distal) regions. Such combination of two flexible haptics improved the stability of the intraocular lens in normal use in an eye. The (aphakic or phakic) intraocular lens is preferably rotationally symmetric around the optical axis.

In some embodiments, the distal border 56 is transverse to (all) the elongated flexible footplates. In some embodiments, the region 52 comprises a proximal border 55 transverse to (all) the elongated flexible footplates. In this way, the elongated flexible footplates 54 are able to curve as a whole when axial and/or radial compression is exerted on the flexible haptic 5, for example when the (aphakic or phakic) intraocular lens is in normal use in an eye. In some embodiments, each of the elongated flexible footplates 54 comprises a proximal extremity $54_1$ and a distal extremity $54_2$, the proximal extremities $54_1$ of the elongated flexible footplates 54 being joined by the proximal border 55, and the distal extremities $54_2$ of the elongated flexible footplates 54 being joined by the distal border 56. The distal border 56 extends preferably circumferentially and/or radially outward relative to the central optical part proposing then a large contact surface and greater stability for the (aphakic or phakic) intraocular lens.

The region 52 can be any sufficient portion of the flexible haptic 5. In particular, as previously, it is possible to consider a flexible haptic 5 comprising a proximal region 51 connected to the (reticulated distal) region 52 along the proximal border 55. Any particular realization of these proximal 51 and distal 52 region can applies mutatis mutandis to this embodiment of the (aphakic or phakic) intraocular lens.

The present application may reference quantities and numbers. Unless specifically stated, such quantities and numbers are not to be considered restrictive, but exemplary of the possible quantities or numbers associated with the present application. Also in this regard, the present application may use the term "plurality" to reference a quantity or number. In this regard, the term "plurality" is meant to be any number that is more than one, for example, two, three, four, five, etc. The terms "about," "approximately," "near," etc., mean plus or minus 5% of the stated value. For the purposes of the present disclosure, the phrase "at least one of A, B, and C," for example, means (A), (B), (C), (A and B), (A and C), (B and C), or (A, B, and C), including all further possible permutations when greater than three elements are listed.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by The embodiments of the invention in which an exclusive property or privilege is claimed are defined as follows:

1. A posterior chamber phakic intraocular lens comprising:
   an anterior surface and a posterior surface;
   a central optical part comprising a lens, and extending radially relative to an optical axis directed from said anterior surface to said posterior surface;
   a peripheral haptic part extending radially outward relative to said central optical part, said peripheral haptic part comprising:
      a proximal portion extending circumferentially around said central optical part;
      a distal portion at least around said proximal portion and comprising a plurality of support elements extending both radially outward and posteriorly relative to said central optical part, said support elements being configured for supporting said phakic intraocular lens on a ciliary zonule when the phakic intraocular lens is in the implantation position in an eye;
   said central optical part and said peripheral haptic part forming a dome;
   at least one flexible haptic comprising:
      a proximal region at least around said proximal portion of said peripheral haptic part;
      a distal region at least around said proximal region and comprising a plurality of distal elongated flexible footplates that extend at least partially radially outward relative to said central optical part, and that border distal cavities extending between said anterior and said posterior surfaces,
   wherein the peripheral haptic part has a thickness, measured in parallel to the optical axis, larger, on average, than that of the flexible haptic,
   a first diameter of said phakic intraocular lens being strictly greater than a second diameter of an optical assembly consisting of said central optical part and said peripheral haptic part, measured perpendicularly to said optical axis;
   at least one of said distal elongated flexible footplates extending substantially between said second and said first diameters;
   said distal region comprising a distal border connecting at least two of said distal elongated flexible footplates, said distal border being configured for stabilizing said phakic intraocular lens into a ciliary sulcus when the phakic intraocular lens is in an implantation position in the eye,
   wherein said proximal region of the at least one flexible haptic comprises a plurality of proximal elongated flexible footplates that extend at least partially radially outward and posteriorly relative to said central optical part, and that border proximal cavities extending between said anterior and said posterior surfaces,
   wherein said proximal elongated flexible footplates of said proximal region are oriented and substantially parallel to a first direction, and/or said distal elongated flexible footplates of said distal region are oriented and substantially parallel to a second direction, and wherein said first direction is transverse to said second direction and said first and said second directions form a smaller angle between them of between 80° and 140°.

2. The posterior chamber phakic intraocular lens according to claim 1, wherein:
   said distal border is transverse to said distal elongated flexible footplates;
   said distal region comprises a proximal border transverse to said distal elongated flexible footplates;
   in such a way that said distal elongated flexible footplates are able to curve as a whole when axial and/or radial compression is exerted on said at least one flexible haptic.

3. The posterior chamber phakic intraocular lens according to claim 2, wherein each of said distal elongated flexible footplates comprises a proximal extremity and a distal extremity, the proximal extremities of said distal elongated flexible footplates being joined by said proximal border, and the distal extremities of said distal elongated flexible footplates being joined by said distal border.

4. The posterior chamber phakic intraocular lens according to claim 1, wherein said distal border extends both circumferentially and radially outward relative to said central optical part.

5. The posterior chamber phakic intraocular lens according to claim 1, wherein said distal border comprises smooth ripples arranged to hook smoothly into a ciliary sulcus when said phakic intraocular lens is in the implantation position in the eye.

6. The posterior chamber phakic intraocular lens according to claim 1, wherein said distal cavities are open cavities.

7. The posterior chamber phakic intraocular lens according to claim 1, wherein said distal elongated flexible footplates are configured for extending substantially along a plane whose normal vector forms an angle comprised between −15° and 15° with said optical axis.

8. The posterior chamber phakic intraocular lens according to claim 7, wherein the area of said distal cavities measured in said plane is at least twice greater than the area of said distal elongated flexible footplates measured in said plane.

9. The posterior chamber phakic intraocular lens according to claim 1, wherein said proximal region extends radially outward and posteriorly relative to said central optical part, between two of said support elements.

10. The posterior chamber phakic intraocular lens according to claim 1, wherein said distal region and said proximal region share a common connecting border transverse to the distal elongated flexible footplates of said distal region and to the proximal elongated flexible footplates of said proximal region, in such a way that said proximal elongated flexible footplates of said proximal region are able to curve as a whole when axial and/or radial compression is exerted on said at least one flexible haptic.

11. The posterior chamber phakic intraocular lens according to claim 10, wherein said common connecting border extends substantially circumferentially around said central optical part, and has a shape of an arc of a circle of said second diameter.

12. The posterior chamber phakic intraocular lens according to claim 1, wherein said lens comprises:
   two such flexible haptics oriented and diametrically opposed; and
   four such support elements oriented according to diagonals of a planar rectangle.

13. The posterior chamber phakic intraocular lens according to claim 1, wherein the lens is shape invariant under a rotation of 180° around said optical axis.

14. The posterior chamber phakic intraocular lens according to claim 1, wherein:
said first diameter is comprised between 12.5 and 14.5 mm;
said second diameter is comprised between 11 and 12 mm.

15. The posterior chamber phakic intraocular lens according to claim 1, wherein a radius of curvature of a smooth posterior surface of said dome is comprised between 8 and 10 mm.

16. The posterior chamber phakic intraocular lens according to claim 1, wherein a smooth posterior surface of said dome is concave.

17. The posterior chamber phakic intraocular lens according to claim 1, wherein said lens comprises a flexible and biocompatible material comprising between 20 and 45% water, and having a Young modulus of less than 1 GPa.

18. The posterior chamber phakic intraocular lens according to claim 1, wherein said central optical part comprises a through bore extending between said anterior and said posterior surfaces and arranged to allow a fluid flow.

19. The posterior chamber phakic intraocular lens according to claim 1, wherein said lens consists in a monofocal lens that allows at least one correction among: a correction of myopia, a correction of hypermetropia, a correction of presbyopia, and a correction of corneal astigmatism.

20. The posterior chamber phakic intraocular lens according to claim 1, wherein said lens consists in a lens at extended refractive or diffractive depth of focus.

* * * * *